United States Patent [19]

Sportoletti et al.

[11] 4,405,643
[45] Sep. 20, 1983

[54] TREATMENT OF ACUTE PULMONARY EDEMA WITH ARGININE ESTERS

[75] Inventors: Giancarlo Sportoletti; Alessandro Baglioni, both of Milan, Italy

[73] Assignee: Italfarmaco S.p.A., Milan, Italy

[21] Appl. No.: 296,830

[22] Filed: Aug. 27, 1981

Related U.S. Application Data

[62] Division of Ser. No. 162,008, Jun. 23, 1980, Pat. No. 4,308,280.

[30] Foreign Application Priority Data

Dec. 28, 1979 [IT] Italy ................................ 28416 A/79

[51] Int. Cl.$^3$ ............................................. A61K 31/22
[52] U.S. Cl. .................................... 424/311; 424/319; 424/10
[58] Field of Search ........................... 424/311, 319, 10

[56] References Cited

PUBLICATIONS

The Pharmacological Basis of Therapeutics 6th ed. MacMillan Pub. Co., NY Goodman et al., p. 870, 1980.

*Primary Examiner*—Sam Rosen
*Assistant Examiner*—John Rollins, Jr.
*Attorney, Agent, or Firm*—Bucknam and Archer

[57] ABSTRACT

Pharmaceutical compositions for use in the relief of acute pulmonary edema, different types of shock including anaphylactic shock, shock induced by bacterial endotoxins, and hyperfibrinolysis induced by substances which activate plasminogen, consist of solutions of an ester of L-arginine with an aliphatic alcohol in water at a pH between 5.5 and 8.5. The compositions may be provided in unit dosage form containing 0.25–100 mg of active substance per kilogram of body weight of the subject in need of treatment and are administered through the parenteral route. The esters may be provided in the form of a salt with a pharmaceutically acceptable organic or inorganic acid. The esters may be with methyl or ethyl alcohol. The compositions are more effective than aspirin and aprotinin.

1 Claim, No Drawings

TREATMENT OF ACUTE PULMONARY EDEMA WITH ARGININE ESTERS

This is a division of application Ser. No. 162,008 filed June 23, 1980, now U.S. Pat. No. 4,308,280.

The present invention relates to novel therapeutic composition, particularly useful against acute pulmonary edema, shock caused by bacterial endotoxins, hyperfibrinolysis and anaphylactic shock. More specifically, the present invention relates to esters of L-arginine.

Many esters of L-arginine are known, such as for instance, esters with aliphatic alcohols which have the general formula:

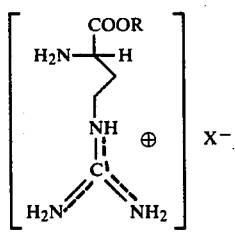

in which X is an organic or inorganic pharmaceutically compatible anion; R is an alkyl group.

These esters with aliphatic alcohols are obtained by esterification of L-arginine by way of the methods which have been reported in the literature such as, for instance, reaction of L-arginine with an aliphatic alcohol which has been previously saturated with dry gaseous hydrogen chloride, or esterification by removal of water by azeotropic distillation or by reaction with an alcohol in the presence of thionyl chloride or similar methods. These esters, for instance in the form of the hydrochloride salts, are stable in the solid state and it is possible to prepare solutions from the esters at a neutral or slightly acidic pH. The solutions are stable for a very long period of time.

It has now been found, surprisingly, that the esters of arginine with aliphatic alcohols and their salts exhibit valuable therapeutic properties in the relief of some pathological condition. The material to be administered by the parenteral route consists of an aqueous solution of pH between 5.5 and 8.5, and contains the cation of the ester of arginine and an inorganic or organic anion in a molar ratio which may be 1:1 or in a different molar ratio. More specifically, the esters and their corresponding salts exhibit inhibitory action with respect to acute pulmonary edema and increase the life expectancy in the case of shock syndrome resulting from a variety of causes, such as bacterial endotoxins or endotoxins of immunitary type.

It has also been found that the esters of L-arginine exhibit valuable activity in vivo in the hyperfibrinolytic syndrome caused by administration of urokinase. It should be noted that all these therapeutic effects are obtained with dosages and by administration routes which do not cause significant toxic effects and that, in general, the toxicity of all these substances is very low. In view of the dosage, the administration routes and, in general, the manner with which the effects on the animals are obtained, these substances are also useful in human therapy in the treatment of pathological conditions of the type mentioned hereinabove.

The activity of the pharmaceutical compositions of the present invention is demonstrated by the experimental results summarized hereinbelow.

Protection Against Pulmonary Edema

The method of A. M. Rothschild and A. Castania (Arch. Pharmacol., 295, 177 (1976)), has been used to develop the acute edema in the lungs and substances of known therapeutic activity have been used for comparison purpose.

For the test, male albino rats of Wistar type of average weight 250–350 grams, have been used for the test. The rats were stabilized for a period of ten days at a temperature of 21°±1° C., under conditions of controlled diet and water "ad libitum". Prior to the test, the animals were divided into groups of ten for the purpose of achieving good randomization. Each dose was tried on three groups of animals. The animals were anesthetized with pentobarbital in a dose of 30 mg/kg at the beginning of the test. After the animals were in complete narcosis, the following substances were administered by the parenteral route:

1. to the animals as controls, physiological saline solution in the amount of 1 ml/kg,
2. to the animals in the test, a solution of the substance being tested in physiological saline solution in the amount of 1 ml/kg in the doses reported hereinbelow in the table.

After a period of 15 minutes, for the purpose of determining the protective activity of the substances, adrenaline was administered in the amount of 16 γ/kg by the endovenous route and in physiological saline solution, for the purpose of causing acute edema.

After five minutes, the animals were killed by removal of the head, the lungs were removed and the weight of the lungs were determined. The results of the test are reported in Table 1 hereinbelow, together with the concentration of the substances and the relative inhibition of edema in percent. The results are discussed at the end of the tables.

TABLE 1

| COMPOUND | DOSE* | % INHIBITION OF EDEMA |
|---|---|---|
| Physiological saline solution 1 ml/kg + adrenaline | — | 0.00 |
| Aspirin | 1 | 32.2 |
| " | 2.5 | 36.9 |
| " | 5 | 48.2 |
| " | 10 | 54.3 |
| " | 20 | 19.6 |
| Aprotinin** | 30 | 17.3 |
| " | 100 | 36.5 |
| " | 300 | 54.5 |
| " | 1000 | 42.7 |
| L-A.M.*** | 1 | 21.2 |
| " | 2.5 | 27.4 |
| " | 5 | 29.0 |
| " | 10 | 55.7 |
| " | 20 | 15.7 |
| D-A.M.**** | 1 | 16.8 |
| " | 2.5 | 11.7 |
| " | 5 | 15.4 |
| " | 10 | 4.4 |
| " | 20 | 6.4 |
| L-A.E.***** | 0.1 | 3.4 |
| " | 0.25 | 32.2 |
| " | 0.5 | 33.3 |
| " | 1 | 55.7 |
| " | 2.5 | 47.9 |
| " | 5 | 41.0 |
| " | 10 | 38.9 |
| " | 20 | 39.7 |
| D-A.E.****** | 0.1 | 7 |

TABLE 1-continued

| COMPOUND | DOSE* | % INHIBITION OF EDEMA |
|---|---|---|
| " | 0.25 | 11 |
| " | 0.5 | 3 |
| " | 1.0 | 4.2 |
| " | 2.5 | 7 |
| " | 5.0 | 5.3 |
| " | 10 | 6 |
| " | 20 | 2.5 |
| L-Arginine.2HCl | 1 | 7 |
| " | 2.5 | 9 |
| " | 5 | 11 |
| " | 10 | 10.1 |
| " | 20 | 13.1 |
| Ethanol | 0.08 | 7 |
| " | 0.8 | 12 |
| " | 2 | 15 |
| " | 4 | 14.7 |
| " | 8 | 16 |
| " | 16 | 15.9 |
| Methanol | 0.08 | 2.3 |
| " | 0.8 | 5 |
| " | 2 | 12 |
| " | 4 | 6 |
| " | 8 | 15 |
| " | 16 | 15 |
| L-Arginine.2HCl + Ethanol | 1 + 0.08 | 10 |
| " | 2.5 + 0.8 | 9 |
| " | 5 + 2 | 5.3 |
| " | 10 + 4 | 7.2 |
| " | 20 + 8 | 4.6 |
| L-Arginine.2HCl + Methanol | 1 + 0.08 | 11.4 |
| " | 2.5 + 0.8 | 7.2 |
| " | 5 + 2 | 9.5 |
| " | 10 + 4 | 8.1 |
| " | 20 + 8 | 6 |

*in mg/kg except in the case of aprotinin, the numbers indicate U.I.K./kg. that is the inhibitory unit of Kunitz.
**the commercial product of the pharmaceutical composition marketed under the name "Trasylol" by Farbenfabriken Bayer has been used.
***L-A.M. = L-Arginine methyl ester hydrochloride.
****D-A.M. = D-Arginine methyl ester hydrochloride.
*****L-A.E. = L-Arginine ethyl ester hydrochloride.
******D-A.E. = D-Arginine ethyl ester hydrochloride.

Protection Against Shock Caused By Endotoxins

Endotoxin-induced shock has been produced according to the method reported by A. Bertelli and L. Donati, in the publication "The Influence of Some Enzymes and Enzymes Inhibitors in Shock", published in "SHOCK Biochemical, Pharmaceutical and Clinical Aspects"; A. Bertelli and N. Back Editors, Advances in Experimental Medicine and Biology; Volume 9, Plenum Press New York - London 1970, page 215. By way of comparison, there has been used a substance of well known therapeutical activity, specifically aprotinine, the commercial products marketed by Farbenfabriken Bayer, under the name "Trasylol". Male rats of Wistar type of 120 grams by weight ±10 have been used. The rats were previously stabilized for a period of ten days at a temperature of 21°±1° C. under a controlled diet and water "ad libitum". Twenty-four hours prior to the test, the animals were divided in groups of ten for the purpose of achieving randomization. Every single dose has been tried on six groups of animals.

Lipopolysaccharide B from S. Enteritidis (Difco Labs.) was used as the endotoxin. This substance was administered in the dose of 10 mg/kg by the endoperitoneal route, one hour after administration of the substance being administered by the parenteral route or in the form of a physiological solution in equal volume per kilogram to the animals being used as control.

The mortality in percent was determined in the animals being tested as compared with the controls after twenty-four hours. The results are reported in Table 2 hereinbelow.

TABLE 2

| COMPOUND | DOSE | % MORTALITY |
|---|---|---|
| Physiological Saline Solution | — | 70.9 |
| Aprotinin | 1000 | 50.0 |
| " | 3000 | 65.0 |
| " | 10000 | 65.0 |
| " | 100000 | 93.3 |
| L-A.M. | 5 | 55.0 |
| " | 10 | 50.0 |
| " | 20 | 40.0 |
| " | 50 | 28.0 |
| D-A.M. | 5 | 71.2 |
| " | 10 | 68.5 |
| " | 20 | 69 |
| " | 50 | 73 |
| L-A.E. | 5 | 51.3 |
| " | 10 | 48.2 |
| " | 20 | 37.5 |
| " | 50 | 25.0 |
| D-A.E. | 5 | 72 |
| " | 10 | 67 |
| " | 20 | 69.3 |
| " | 50 | 71 |
| L-Arginine.2HCl | 5 | 69 |
| " | 10 | 73 |
| " | 20 | 71 |
| " | 50 | 78 |
| Methanol | 2 | 76 |
| " | 4 | 72 |
| " | 8 | 74 |
| Ethanol | 2 | 67 |
| " | 4 | 69 |
| " | 8 | 73 |
| L-Arginine.2HCl + Methanol | 4 + 0.61 | 73 |
| " | 8 + 1.23 | 71 |
| " | 16 + 2.46 | 75 |
| L-Arginine.2HCl + Ethanol | 4 + 1.06 | 69 |
| " | 8 + 2.12 | 71 |
| " | 16 + 4.24 | 74 |

The abbreviations are explained under Table 1. Also in this case, the doses of aprotinin are expressed in terms of U.I.K./kg.

Protection Against Anaphylactic Shock

The anaphylactic shock has been induced according to the method of S. M. Feinberg, M. Pharmacol. Exp. Therapeut., 99, 195 (1950). There have been used male albino guinea pigs of average weight, 350±20 grams previously stabilized for a period of ten days at a temperature of 21°±1° C., under conditions of controlled diet and water "ad libitum". Three days before the beginning of the experiment, the animals are divided in groups of ten for the purpose of achieving good randomization. Each single dose has been tried on three groups of animals.

The sensitization has been carried out by administration of 1 ml/guinea pig through the endovenous route of horse serum, (whole serum, not treated with preservatives) diluted 1:10 in physiological saline solution. After 14 days, the solutions of the substances being tested and the samples of physiological solutions for use with the controls are administered through the parenteral route. Simultaneously, 1 ml/guinea pig of horse serum, undiluted is administered, this substance being used as the agent which prompts the anaphylaxis. The percentage of mortality is determined after 12 hours. The results are reported in Table 3.

TABLE 3

| COMPOUND | DOSE | % MORTALITY |
|---|---|---|
| Physiological Saline Solution | — | 80 |
| Aprotinin | 3000 | 40 |
| " | 10000 | 55 |

TABLE 3-continued

| COMPOUND | DOSE | % MORTALITY |
|---|---|---|
| " | 100000 | 80 |
| L-A.M. | 10 | 40.5 |
| " | 20 | 27 |
| " | 50 | 12.5 |
| D-A.M. | 10 | 78.8 |
| " | 20 | 81.0 |
| " | 50 | 76.3 |
| L-A.E. | 10 | 35 |
| " | 20 | 23 |
| " | 50 | 9.5 |
| D-A.E. | 10 | 76.7 |
| " | 20 | 79.4 |
| " | 50 | 81.0 |
| L-Arginine.2HCl | 10 | 78.5 |
| " | 20 | 76.3 |
| " | 50 | 80 |
| Methanol | 2 | 76.6 |
| " | 4 | 79.4 |
| " | 8 | 81 |
| Ethanol | 2 | 76.4 |
| " | 4 | 74 |
| " | 8 | 76.5 |
| L-Arginine.2HCl + Methanol | 4 + 0.61 | 77.3 |
| " | 8 + 1.23 | 76.3 |
| " | 16 + 2.46 | 81.0 |
| L-Arginine.2HCl + Ethanol | 4 + 1.06 | 75.8 |
| " | 8 + 2.12 | 73.2 |
| " | 16 + 4.24 | 77.0 |

For the dosage and abbreviations, see the description in Table 1.

Inhibition of Hyperfibrinolysis

The induction of hyperfibrinolysis state is caused by administration of urokinase. The determination of the inhibition is carried out by determination of the F.D.P. value, that is Fibrin Degradation Products, according to the procedure of J. Hawiger et al, J. Lab. Clin. Med. 75, 93 (1970), by means of the staphylococcal clumping test (Boehringer Mannheim GmbH test).

There are used Wistar rats of 300 grams ±10 by weight previously stabilized for a period of ten days at a temperature of 21°±1° C., under conditions of controlled diet and water "ad libitum". Twenty-four hours prior to the beginning of the experiment, the animals are divided in groups of ten for the purpose of achieving randomization. Each individual dose is tried on three groups of animals.

At the beginning of the test, zero time, the compounds being tested are administered through the parenteral route. In the case of the control animals, at the same time an equal volume of a physiological saline solution is administered except that some blood is removed by means of a cardiac puncture, for the purpose of determining the basal fibrinolytic activity. After 30 minutes, human urokinase (the composition marketed by Ukidan-Serono) is administered intravenously in the amount of 2500 U.I/rat. After an additional period of ten minutes, blood is removed by means of a cardiac puncture for the final determination of F.D.P., a determination which is expressed in milliliters. The results thus obtained are summarized in Table 4.

TABLE 4

| COMPOUND | DOSE | F.D.P. |
|---|---|---|
| — | — | 0.26 Basal |
| Physiological Saline Solution | — | 3.30 |
| Aprotinin | 1000 | 0.34 |
| " | 3000 | 0.29 |
| " | 10000 | 0.30 |
| Tranexamic Acid | 5 | 0.58 |
| " | 10 | 0.39 |
| " | 20 | 0.33 |

TABLE 4-continued

| COMPOUND | DOSE | F.D.P. |
|---|---|---|
| L-A.M. | 5 | 0.48 |
| " | 10 | 0.30 |
| " | 20 | 0.25 |
| D-A.M. | 5 | 3.10 |
| " | 10 | 3.03 |
| " | 20 | 3.16 |
| L-A.E. | 5 | 0.50 |
| " | 10 | 0.33 |
| " | 20 | 0.27 |
| D-A.E. | 5 | 3.20 |
| " | 10 | 3.16 |
| " | 20 | 3.19 |
| L-Arginine.2HCl | 5 | 3.28 |
| " | 10 | 2.96 |
| " | 20 | 3.15 |
| Methanol | 2 | 3.02 |
| " | 4 | 3.12 |
| " | 8 | 3.27 |
| Ethanol | 2 | 3.06 |
| " | 4 | 2.95 |
| " | 8 | 3.11 |
| L-Arginine.2HCl + Methanol | 4 + 0.61 | 3.00 |
| " | 8 + 1.23 | 3.12 |
| " | 16 + 2.46 | 3.20 |
| L-Arginine.2HCl + Ethanol | 4 + 1.06 | 2.98 |
| " | 8 + 2.12 | 2.99 |
| " | 16 + 4.24 | 3.20 |

For dosage and abbreviations see description under Table 1.
Tranexamic acid is trans-4-(aminomethyl)cyclohexancarboxylic acid.

The data reported in Tables 1 through 4 hereinabove demonstrate the significant therapeutic effect of the ethyl or methyl esters of arginine at the test dosage and the specificity of the activity with reference to the structure of the compound and also its stereoisomerism. In fact, insignificant effects and effects comparable to the animals being treated as control with physiological saline solution, have been obtained by administration to the animals of arginine itself or the alcohols by themselves or mixtures of arginine and the alcohols or the esters of D-arginine.

The toxicity of esters of L-arginine, the therapeutic activity of which has been demonstrated in the examples hereinabove, has been tested in two aniaml species, that is in mice, intravenously and in rats, both intravenously and endoperitonally. The results of LD-50 mg/kg are as follows:

Species: male mouse albino Swiss of average weight 22 grams ±1 route of administration: endovenously LD-50: 315.6 mg/kg (L.F.=276.5–360.2)

Species: male albino Wistar rat of average weight 180 ±10 grams route of administration: endovenously LD-50: 431.73 mg/kg (L.F.=374.2–498.0) route of administration: endoperitonally LD-50: 1111.1 mg/kg (L.F.=1002.9–1230.8).

It should be noted that the values of toxicity are in a range substantially higher with respect to the dosage being used for therapeutic purposes.

With the dosage reported hereinabove and in accordance with the route of administration as described hereinabove, the administration of the substances in healthy animals has not caused mortality nor has it caused apparent symptoms of toxicity. The data reported in Tables 1–4 demonstrate the therapeutic value of the pharmaceutical compositions according to the invention.

What is claimed is:

1. A method of protecting an animal from pulmonary edema caused by adrenaline which consists of administering parenterally to said animal the ethyl or methyl ester of L-arginine as the hydrochloride salt in an aqueous solution at a pH between 5.5 and 8.5 in an amount effective to protect said animal from edema.

* * * * *